(12) United States Patent
Barsoum

(10) Patent No.: US 9,788,880 B2
(45) Date of Patent: Oct. 17, 2017

(54) METHOD AND APPARATUS FOR PROVIDING A RELATIVE LOCATION INDICATION DURING A SURGICAL PROCEDURE

(71) Applicant: THE CLEVELAND CLINIC FOUNDATION, Cleveland, OH (US)

(72) Inventor: Wael K. Barsoum, Bay Village, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 442 days.

(21) Appl. No.: 14/511,954

(22) Filed: Oct. 10, 2014

(65) Prior Publication Data

US 2015/0045796 A1   Feb. 12, 2015

Related U.S. Application Data

(62) Division of application No. 13/178,324, filed on Jul. 7, 2011, now Pat. No. 8,882,770.

(60) Provisional application No. 61/362,722, filed on Jul. 9, 2010.

(51) Int. Cl.
| | | |
|---|---|---|
| A61B 17/88 | (2006.01) | |
| A61B 17/16 | (2006.01) | |
| A61B 17/17 | (2006.01) | |
| A61B 90/00 | (2016.01) | |

(52) U.S. Cl.
CPC ........ *A61B 17/8897* (2013.01); *A61B 17/16* (2013.01); *A61B 17/1746* (2013.01); *A61B 90/06* (2016.02); *A61B 2090/036* (2016.02); *A61B 2090/037* (2016.02); *A61B 2090/062* (2016.02)

(58) Field of Classification Search
CPC .................................................. A61B 17/8897
See application file for complete search history.

(56) References Cited

U.S. PATENT DOCUMENTS

| | | | | |
|---|---|---|---|---|
| 3,867,932 A | * | 2/1975 | Huene | A61B 17/17 606/104 |
| 4,345,602 A | | 8/1982 | Yoshimura et al. | |
| 4,365,958 A | | 12/1982 | Vlock | |
| 5,242,444 A | | 9/1993 | MacMillan | |
| 5,895,389 A | * | 4/1999 | Schenk | A61B 17/17 606/102 |
| 5,989,260 A | * | 11/1999 | Yao | A61B 17/1717 606/102 |
| 6,512,958 B1 | | 1/2003 | Swoyer et al. | |
| 7,641,656 B2 | | 1/2010 | Collins et al. | |
| 2002/0077631 A1 | | 6/2002 | Lubbers et al. | |
| 2002/0173794 A1 | * | 11/2002 | Happonen | A61B 17/1655 606/79 |

(Continued)

*Primary Examiner* — Nicholas Woodall
(74) *Attorney, Agent, or Firm* — Norton Rose Fulbright Canada LLP

(57) ABSTRACT

An orthopedic guidewire includes an elongate guidewire body having longitudinally spaced proximal and distal guidewire ends. An engaging feature is located at the distal guidewire end and is configured to selectively engage a bone surface. At least one of a variable diameter and a variable stiffness are along a portion of the guidewire body spaced apart from the engaging feature. A method of providing a relative location indication during a surgical procedure utilizing the orthopedic guidewire is also included.

11 Claims, 1 Drawing Sheet

(56) References Cited

U.S. PATENT DOCUMENTS

| | | |
|---|---|---|
| 2004/0039395 A1 | 2/2004 | Coon et al. |
| 2004/0199166 A1 | 10/2004 | Schmieding et al. |
| 2005/0080443 A1 | 4/2005 | Fallin et al. |
| 2005/0107799 A1 | 5/2005 | Graf et al. |
| 2005/0273107 A1 | 12/2005 | Stevens |
| 2006/0085012 A1 | 4/2006 | Dolan |
| 2008/0051793 A1 | 2/2008 | Erickson et al. |
| 2008/0300600 A1 | 12/2008 | Guelat et al. |
| 2009/0048606 A1 | 2/2009 | Tipirneni et al. |
| 2009/0088768 A1 | 4/2009 | Grant et al. |
| 2009/0228015 A1 | 9/2009 | Ellis et al. |
| 2009/0254094 A1 | 10/2009 | Knapp et al. |
| 2009/0264924 A1 | 10/2009 | Ushiba |
| 2009/0312769 A1 | 12/2009 | Dadd et al. |
| 2010/0063511 A1 | 3/2010 | Plassky et al. |
| 2010/0152740 A1 | 6/2010 | O'Reilly et al. |
| 2013/0072986 A1* | 3/2013 | Robinson ............ A61B 17/8605 606/279 |
| 2014/0276894 A1* | 9/2014 | Ramsay ............. A61B 17/7076 606/104 |
| 2016/0183995 A1* | 6/2016 | Zrinski .................. A61B 17/88 606/96 |

\* cited by examiner

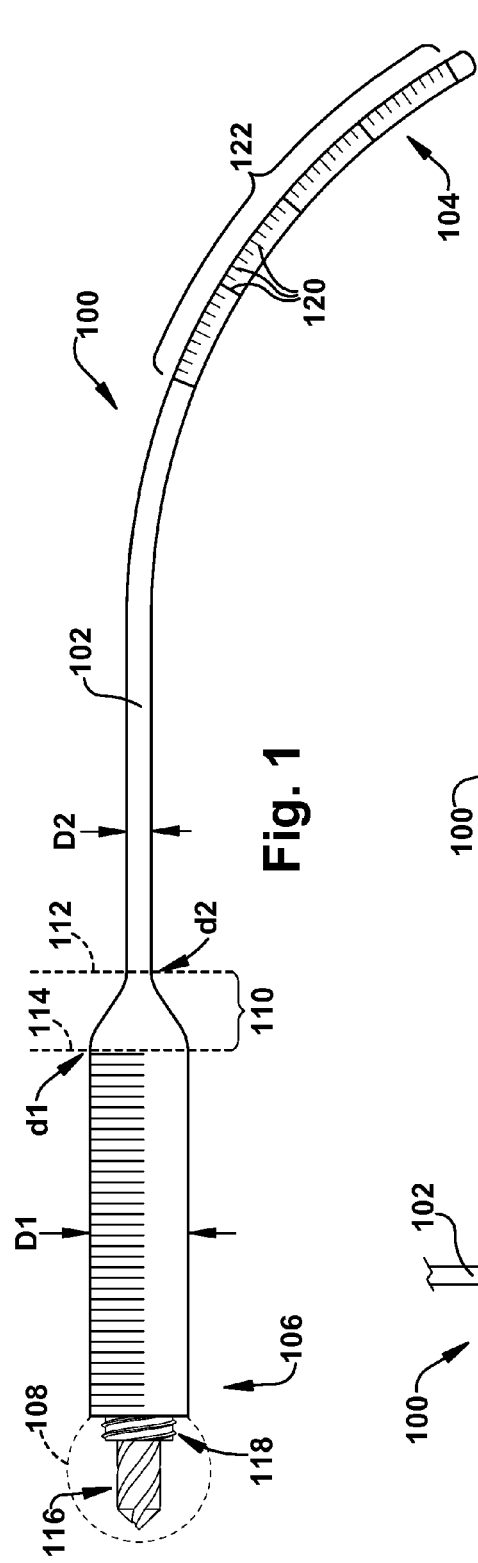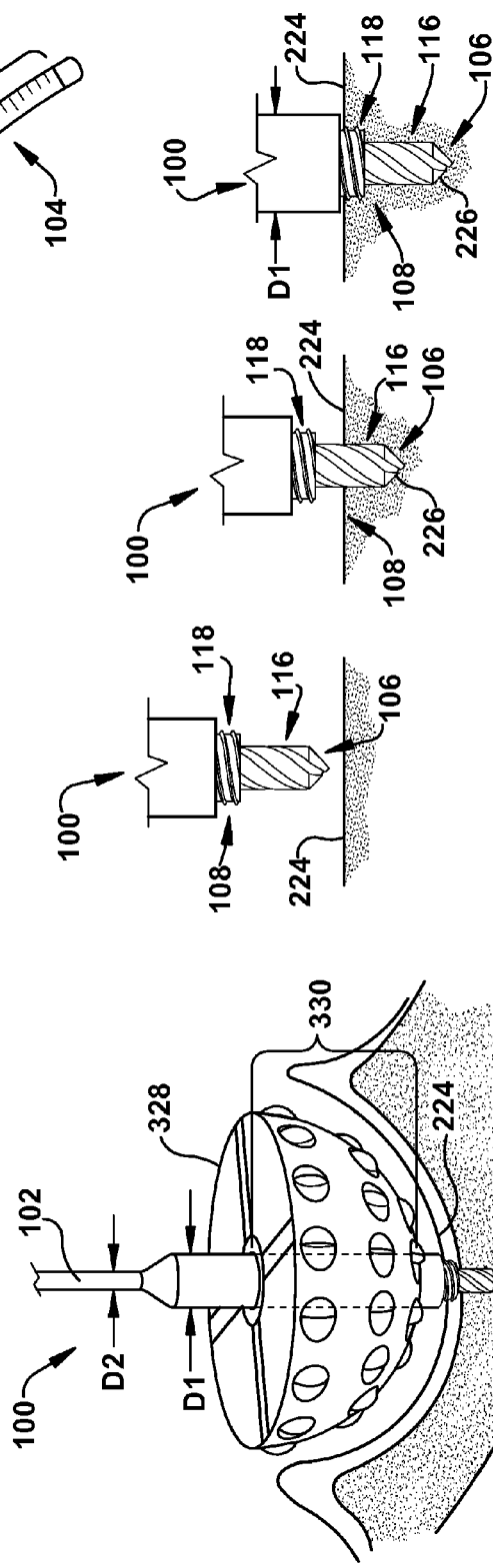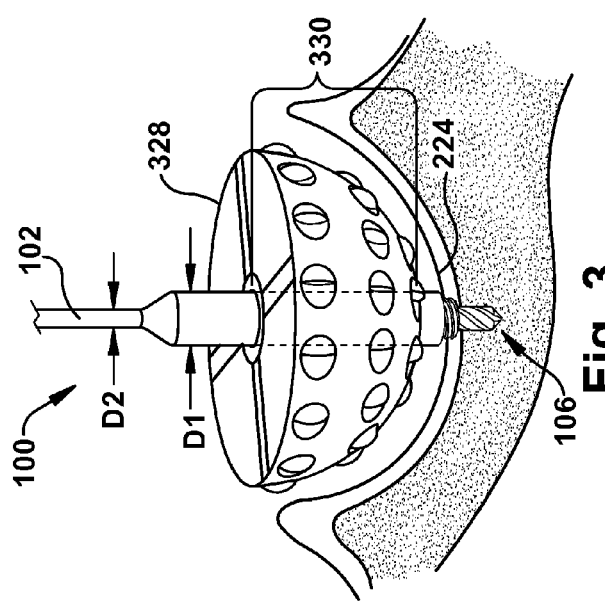

US 9,788,880 B2

METHOD AND APPARATUS FOR PROVIDING A RELATIVE LOCATION INDICATION DURING A SURGICAL PROCEDURE

RELATED APPLICATION

This application is a divisional application of U.S. Non-Provisional application Ser. No. 13/178,324 which claims priority from U.S. Provisional Application No. 61/362,722, filed 9 Jul. 2010, the subject matter of which is incorporated herein by reference.

TECHNICAL FIELD

The present invention relates to an apparatus and method for providing a relative location indication during a surgical procedure and, more particularly, to an orthopedic guidewire and method for use.

BACKGROUND OF THE INVENTION

During a surgical procedure, it can be difficult to maintain a steady frame of reference with respect to the patient tissue within the surgical site. For example, the surgery may modify the patient tissue, the patient tissue may move within the patient's body, blood may obscure the patient tissue, local anatomic conditions may require that the patient tissue may be viewed or manipulated at an awkward angle for the surgeon, or the like. In addition, the patient tissue may be slippery or unstable within the surgical site.

Accordingly, a guide pin or guidewire may be temporarily engaged with the patient tissue and protrude therefrom to provide a landmark to orient the user during the surgical procedure. Particularly when the patient tissue of concern is bony or otherwise able to firmly engage and support a rigid structure, an orthopedic guidewire may be attached to the patient tissue to provide a location orientation relative to the patient tissue.

Additionally, a sufficiently sturdy or rigid guidewire may be used to physically guide a tool to a desired location on the patient tissue. For example, a reamer could have a center hole that fits over the rigid guidewire for reaming an area of the patient tissue concentrically surrounding the guidewire.

SUMMARY OF THE INVENTION

In an embodiment of the present invention, an orthopedic guidewire is described. An elongate guidewire body has longitudinally spaced proximal and distal guidewire ends. An engaging feature is located at the distal guidewire end and is configured to selectively engage a bone surface. At least one of a variable diameter and a variable stiffness are along a portion of the guidewire body spaced apart from the engaging feature.

In an embodiment of the present invention, an orthopedic guidewire for providing a relative location indication during a surgical procedure is described. An elongate guidewire body has longitudinally spaced proximal and distal guidewire ends. The guidewire body has a first diameter at a portion of the guidewire body proximally adjacent to the engaging feature and a second diameter at a portion of the guidewire body distally adjacent to the proximal guidewire end. The first diameter is greater than the second diameter. An engaging feature is located at the distal guidewire end and is configured to engage a bone surface. The engaging feature includes a cutting portion and a stabilizing portion. The cutting portion is located distally from, and longitudinally adjacent to, the stabilizing portion.

In an embodiment of the present invention, a method of providing a relative location indication during a surgical procedure is described. An orthopedic guidewire including an elongate guidewire body having longitudinally spaced proximal and distal guidewire ends, and an engaging feature located at the distal guidewire end and configured to selectively engage a bone surface is provided. The guidewire body has at least one of a variable diameter and a variable stiffness along a portion of the guidewire body spaced apart from the engaging feature. The guidewire is arranged into a predetermined configuration with respect to the bone surface. The engaging feature is placed into contact with the bone surface according to the predetermined configuration. The bone surface is engaged with the engaging feature. The guidewire is maintained in the predetermined configuration for a desired time period. The maintained guidewire is utilized as a relative location indicator during the surgical procedure.

BRIEF DESCRIPTION OF THE DRAWINGS

For a better understanding of the invention, reference may be made to the accompanying drawings, in which:

FIG. 1 is a side view of one embodiment of the present invention;

FIGS. 2A-2C are partial schematic side views depicting a sequence of operation of the embodiment of FIG. 1; and FIG. 3 is a schematic side view of an example use environment for the embodiment of FIG. 1.

DESCRIPTION OF EMBODIMENTS

In accordance with the present invention, FIG. 1 depicts an orthopedic guidewire 100 for providing a relative location indication during a surgical procedure. An elongate guidewire body 102 has longitudinally spaced proximal and distal guidewire ends 104 and 106, respectively. The term "longitudinal" is used herein to refer to a direction defined by the length of the guidewire body 102, which is substantially horizontal in the orientation of FIG. 1. The term "lateral" is used herein to refer to a direction which is substantially perpendicular to the longitudinal direction; the lateral direction in FIG. 1 is into and out of the plane of the page.

An engaging feature 108 is located at the distal guidewire end 106 and is configured to selectively engage a patient tissue (not shown in FIG. 1). For clarity in the below description, the surface of the patient tissue will be described as a bone surface, such as that of an acetabulum or a glenoid vault, but may be any suitable patient tissue such as, but not limited to, cartilage, muscle, ligament, tendon, adipose, or any other type of tissue. "Patient tissue" will still be used herein to reference a volume underneath the bone surface.

The orthopedic guidewire 100 has at least one of a variable diameter and a variable stiffness along a portion of the guidewire body spaced apart from the engaging feature 108. For example, and as shown in FIG. 1, the guidewire body 102 may have a first diameter D1 at a portion of the guidewire body proximally adjacent to the engaging feature 108 and a second diameter D2 at a portion of the guidewire body distally adjacent to the proximal guidewire end 104. The first diameter D1, as depicted in the Figures, is greater than the second diameter D2. Though "diameter" is used herein for simplicity, there is no requirement that the guidewire body 102 have a circular cross-section. Instead, any portion of the orthopedic guidewire 100 can have any desired curvilinear, curved, rectilinear, or other suitable cross-sectional shape. When the cross-section is non-circular, "diameter" (as used herein) will instead refer to any similarly used measurement across at least a portion of the cross-section, as will be understood by one of ordinary skill in the art. As another example, though not separately shown in the Figures, the orthopedic guidewire 100 may have a first stiffness at a portion of the guidewire body 102 proximally adjacent to the engaging feature 108 and a second stiffness at a portion of the guidewire body distally adjacent to the proximal guidewire end 104, with the first stiffness being greater than the second stiffness. The term "stiffness" is used herein to indicate the resistance of an elastic body to deflection or deformation by an applied force.

One of ordinary skill in the art will realize that the stiffness and diameter of the guidewire body 102 may be, but are not necessarily, linked. For example, when the guidewire body 102 shown in FIG. 1 is made of a single material, the portion of the guidewire body having the greater diameter D1 is likely to be stiffer than the portion of the guidewire body having the smaller diameter D2. However, if different materials are used for the greater diameter D1 portion of the guidewire body 102 and the smaller diameter D2 portion, it is conceivable that the stiffness of the two portions may be substantially the same, or that the stiffness of the greater diameter D1 portion might even be smaller than the stiffness of the smaller diameter D2 portion.

The purpose of the variable stiffness and/or diameter is to provide desired mechanical properties to the orthopedic guidewire 100. For example, it may be desirable for a proximally-located smaller diameter D2 portion of the guidewire body 102 to be flexible and easy to move around as needed during a surgical procedure while a distally-located greater diameter D1 portion of the guidewire body substantially maintains its position with respect to the bone surface. One of ordinary skill in the art may readily provide an orthopedic guidewire 100 having desired diameters and stiffnesses for a particular application of the present invention.

Optionally, the guidewire body 102 may include a transition portion 110, as shown in FIG. 1, having longitudinally separated proximal and distal transition ends 112 and 114, respectively. The guidewire body 102 may have a first diameter d1 at the distal transition end 114 and taper to a second diameter d2 at the proximal transition end, the first diameter d1 being different from the second diameter d2. In the embodiment shown in FIG. 2, the first diameter d1 of the transition portion 110 is substantially equal to the first diameter D1 of the guidewire body 102 and the second diameter d2 of the transition portion is substantially equal to the second diameter D2 of the guidewire body. When there is no transition portion 110 present for a variable-diameter guidewire body 102, the shift between guidewire body diameters D1 and D2 could occur in a stepwise fashion instead of the gradual taper provided by the transition portion 110. Whether or not a transition portion 110 is provided, the portion of the guidewire body 102 having the greater diameter D1 and the portion of the guidewire body having the smaller diameter D2 may have any desired lengths and are not restricted to the roughly one-third D1 and two-thirds D2 ratio of the total orthopedic guidewire 100 length shown in FIG. 1.

The engaging portion 108 may include both a cutting portion 116 and a stabilizing portion 118, with the cutting portion located longitudinally adjacent the stabilizing portion. The cutting portion 116 may be located distally from the stabilizing portion 118. Optionally, and as shown in the Figures, the cutting portion 116 and stabilizing portion 118 may be in direct contact.

The cutting portion 116 of the orthopedic guidewire 100 is configured to create a guidewire-holding aperture in the bone surface and may be designed to carry bone chips out of the guidewire-holding aperture. For example, the cutting portion may be a tapered drill bit having a fluted internal cutting thread, as shown in the Figures.

The stabilizing portion 118 of the orthopedic guidewire 100 is configured to maintain the orthopedic guidewire's 100 engagement with the bone surface. For example, the stabilizing portion 118 may have an external thread, as shown in the Figures. This external thread of the stabilizing portion 118 may have a coarser pitch and/or a different profile than a pitch and/or profile of the cutting thread of the cutting portion 116, in order to act as a braking force on the advancement of the cutting portion 116 and assist with anchoring the orthopedic guidewire 100 to the bone surface and/or patient tissue. That is, the cutting portion 116 may cut and remove material (via action of the cutting thread) to form a guidewire-holding aperture, and the stabilizing portion 118 may then engage with the sidewalls of the guidewire-holding aperture in a gripping fashion to anchor the orthopedic guidewire 100 without removing additional material and thereby enlarging the diameter or width of the guidewire-holding aperture.

As an alternative (not shown), the engaging portion 108 of the orthopedic guidewire 100 may include a single structure which serves as both a cutting portion 116 and a stabilizing portion 118. For example, the engaging portion 108 may resemble a common wood screw, with a shaft tapering to a pointed tip and an external thread protruding from, and spiraling around, at least a portion of the shaft. This or any other suitable engaging portion 108 may be used without harm to the present invention.

At least a portion of the guidewire body 102 may include at least one gauge marking 120, with a plurality of gauge markings 120 forming an indicator scale or distance scale 122 on the orthopedic guidewire 100 shown in FIG. 1. The distance scale 122 may be helpful to the user in gauging a relative longitudinal distance from the bone surface when the orthopedic guidewire 100 is maintained in engagement with the bone surface.

FIGS. 2A-2C depict a sequence of operation of the orthopedic guidewire 100. In FIG. 2A, the orthopedic guidewire 100 has been arranged in a predetermined configuration with respect to a bone surface 224. For example, a lateral position of the orthopedic guidewire 100 upon the bone surface 224 may be chosen by the user or predetermined using preoperative imaging. The distal guidewire end 106 is placed into contact with the bone surface 224 according to the predetermined configuration.

The bone surface 224 is then contacted and engaged by the engaging feature 108 of the orthopedic guidewire 100, moving the orthopedic guidewire into the position shown in FIG. 2B. Optionally, a pilot hole (not shown) may be prepared in the bone surface 224 in order to mark the predetermined configuration and/or ease the initial penetration of the engaging feature 108 into the bone surface 224.

Because the orthopedic guidewire 100 of the Figures uses a threaded engagement, the described motion and engagement are provided by rotation or twisting of the orthopedic guidewire 100 to "screw" the engaging feature 108 into the bone surface 224 in a screwdriver-like manner. Here, the orthopedic guidewire 100 has been rotated through a first rotation sequence to cause the cutting portion 116 of the engaging feature 108 to penetrate into the bone surface 224, and the cutting portion 116 is cutting into the patient tissue to produce a guidewire-holding aperture 226. During the first rotation sequence, the cutting portion 116 bites into the patient tissue and pulls the orthopedic guidewire 100 distally into the bone surface 224.

Once the cutting portion 116 is substantially through the bone surface 224, the orthopedic guidewire is rotated through a second rotation sequence to cause the stabilizing portion 118 to penetrate into the bone surface 224, into the position shown in FIG. 2C. During the second rotation sequence, the stabilizing portion 118 grabs the sidewalls of the guidewire-holding aperture 226 and resists further distal movement of the orthopedic guidewire 100 into the bone surface 224. Optionally, and as shown in FIG. 2C, a portion of the guidewire body 102 proximally adjacent to the engaging feature 108 has an increased-diameter portion, shown here as the first diameter D1, which is greater than the largest diameter of the engaging feature in the embodiment of the Figures. When present, this arrangement acts as a "stop"; that is, the first diameter D1 of the guidewire body 102 is configured to abut the bone surface 224 and prevent the orthopedic guidewire 100 from moving longitudinally even further distally into the bone surface when the engaging feature 108 has been fully engaged with the bone surface.

Once the orthopedic guidewire 100 has been fully engaged with the bone surface 224 into the installed arrangement shown in FIG. 2C, the orthopedic guidewire can be maintained in that predetermined configuration for a desired time period. Typically, this desired time period will be based upon the need of the user to refer to the installed orthopedic guidewire 100 for relative location indication during the course of the surgical procedure, but it is also contemplated that the orthopedic guidewire may remain in the patient's body after the conclusion of the surgical procedure.

When the installed orthopedic guidewire 100 is being utilized as a relative location indicator during the surgical procedure, the user may perform any of a great number of tasks with the assistance of the orthopedic guidewire. For example, the orthopedic guidewire 100 may be used as an origin point for the user to find desired locations on the bone surface laterally spaced from the orthopedic guidewire. As another example, and when the engaging feature 108 is tightly enough connected to the patient tissue, the orthopedic guidewire 100 could be used as a handle to help manipulate the engaged patient tissue. Moreover, another example use of the orthopedic guidewire 100 might be as an anchor for another structure (not shown) being used in the surgical procedure.

FIG. 3 illustrates yet another example of a manner in which the installed orthopedic guidewire 100 may be utilized as a relative location indicator during the surgical procedure. In FIG. 3, a separately provided orthopedic tool, shown here as a reamer 328, is provided, and the bone surface 224 is shown, by way of example, as an acetabular surface which is being prepared to accept a prosthetic hip component. The proximal guidewire end 104 has been inserted into a guiding aperture 330 which runs down the longitudinal center of the reamer 328. The reamer 328 has been passed over the guidewire body 102 and is being brought into contact with the bone surface 224 in the view of FIG. 3. The reamer 328 in this example is configured to rotate in the lateral plane with the guidewire body 102 as an axis of rotation and thereby ream out the acetabular surface in a desired manner.

The association of the reamer 328 with the orthopedic guidewire 100 illustrates one of the considerations that might dictate the longitudinal locations and absolute diameters of the portions of the guidewire body 102 having the greater and smaller diameters D1 and D2. More specifically, in the example use environment of FIG. 3, the proximal guidewire end 104 may have the smaller diameter D2 to facilitate insertion into the guiding aperture 330 and initial movement of the reamer 328 toward the bony surface 224 along the guidewire body 102. Once the reamer 328 has been guided toward the bony surface 224 by the portion of the guidewire body 102 having the smaller diameter D2, the reamer may encounter the portion of the guidewire body having the greater diameter D1. D1 may be chosen responsive to the diameter of the guiding aperture 330 of the reamer 328 to provide a close fit between the guidewire body 102 and the guiding aperture 330 as shown in FIG. 3, which would tend to steady the reamer 328 as it approaches the bone surface 224 and may be desirable for control of the reaming operation.

As the reamer 328 (or any other separately provided orthopedic tool used during the surgical procedure) moves longitudinally with respect to the orthopedic guidewire 100, the user may determine a relative longitudinal distance of the reamer or other tool with respect to the bone surface 224 by using the distance scale 122. For example, if the user wants to ream three millimeters into the bone surface 224, the position of a longitudinally fixed portion of the reamer 328 could be compared to the distance scale 122 to determine an initial position of the reamer. The reamer 328 could then be actuated to begin the reaming operation (generally by rotating about the guidewire body 102, which is maintained in engagement with the bone surface 224) and moved longitudinally distally until the longitudinally fixed portion of the reamer is located at a point on the distance scale 122 three millimeters below the initial position. One of ordinary skill in the art can readily extrapolate from this description other uses of the installed orthopedic guidewire 100 to indicate relative locations, positions, and changes of position of tools or other structures at and/or near the surgical site in the patient tissue.

Once the user no longer desires to utilize the installed orthopedic guidewire 100 for providing a relative location indication, or any other services (e.g., an anchoring function) during a surgical procedure, the engaging feature 108 is disengaged from the bone surface 224 to release the orthopedic guidewire therefrom. This can be accomplished by "unscrewing" the engaging feature 108 by rotating the guidewire body 102 in a rotation direction opposite that used to engage the bone surface 224, by exerting a proximally-directed longitudinal force to pull the engaging feature straight out of the guidewire-holding aperture 226, or by any other suitable method. The released orthopedic guidewire can then be removed from the area of the surgical procedure.

While aspects of the present invention have been particularly shown and described with reference to the preferred embodiment above, it will be understood by those of ordinary skill in the art that various additional embodiments may be contemplated without departing from the spirit and scope of the present invention. For example, the orthopedic guidewire 100 may be formed of any suitable material or combination of materials, and may be integrally formed as a single piece or assembled from component parts. The engagement of the orthopedic guidewire 100 with the bone surface 224 is being described as a threaded engagement facilitated by rotation of the orthopedic guidewire about a longitudinal axis, but may instead be an interference fit, percussive engagement, or any other desired engaging mechanism. Any number of additional diameters (not shown), larger or smaller than D1 and D2 and arranged in any suitable sequence along the length of the orthopedic guidewire 100, may be provided—e.g., an increased-from-D2-diameter portion may be provided at the proximal guidewire end 104 to assist the user with grasping and manipulating that portion of the orthopedic guidewire. At least a portion of the orthopedic guidewire 100 (e.g., the engaging feature 108) could be frangible and configured to "break off" the rest of the orthopedic guidewire and remain associated with the patient tissue longer than the remaining portion of the orthopedic guidewire. A variety of sizes and configurations of orthopedic guidewires 100 could be provided, with a user choosing the one(s) most desired for a particular use environment. The orthopedic guidewire 100 could be modular in nature, with the user choosing a desired engaging feature 108 (or portions thereof), and one or more guidewire body 102 segments having desired lengths, diameters, materials, stiffnesses, or any other characteristics, then the user can assemble a completed orthopedic guidewire having a desired group of properties for a particular use application. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. A method of providing a relative location indication during a surgical procedure, the method comprising the steps of:
   arranging an orthopedic guidewire into a predetermined configuration with respect to a bone surface, the orthopedic guidewire including an elongate guidewire body having longitudinally spaced proximal and distal guidewire ends, and an engaging feature located at the distal guidewire end and configured to selectively engage the bone surface, the guidewire body having at least one of a variable diameter and a variable stiffness along a portion of the guidewire body spaced apart from the engaging feature;
   placing the engaging feature into contact with the bone surface according to the predetermined configuration;
   engaging the bone surface with the engaging feature;
   maintaining the guidewire in the predetermined configuration for a desired time period;
   utilizing the guidewire as a relative location indicator during at least another step of the surgical procedure, the guidewire being maintained in engagement with the bone surface during the at least another step of the surgical procedure; and
   disengaging the engaging feature from the bone surface to release the guidewire from the bone surface.

2. The method of claim 1, wherein the step of engaging the bone surface with the engaging feature includes the step of using the engaging feature with a cutting portion and a stabilizing portion, the cutting portion located longitudinally adjacent the stabilizing portion.

3. The method of claim 2, wherein the step of engaging the bone surface with the engaging feature includes the steps of:
   rotating the guidewire through a first rotation sequence to cause the cutting portion to penetrate into the bone surface;
   pulling the guidewire distally into the bone surface through action of the cutting portion;
   rotating the guidewire through a second rotation sequence to cause the stabilizing portion to penetrate into the bone surface; and
   resisting distal movement of the guidewire into the bone surface through action of the stabilizing portion.

4. The method of claim 1, wherein the step of placing the engaging feature into contact with the bone surface according to the predetermined configuration includes the step of placing the engaging feature into contact with a prepared pilot hole in the bone surface.

5. The method of claim 1, wherein the step of utilizing the maintained guidewire as a relative location indicator during the surgical procedure includes at least one of the steps of:
   inserting the proximal guidewire end into a guiding aperture of a separately provided orthopedic tool; and
   passing the orthopedic tool over the guidewire body and into contact with the bone surface.

6. The method of claim 1, including the step of determining a relative longitudinal distance with respect to the bone surface by using an indicator scale on the maintained guidewire.

7. The method of claim 1, including the step of resisting distal longitudinal movement of the guidewire with respect to the bone surface by bringing an increased-diameter feature of the guidewire into contact with the bone surface.

8. The method of claim 1, wherein utilizing the guidewire as the relative location indicator includes engaging an orthopedic tool onto the guidewire for the orthopedic tool to contact the bone surface.

9. The method of claim 8, wherein engaging the orthopedic tool onto the guidewire includes engaging a reamer onto the guidewire, the reamer being rotated about an axis of rotation defined by the guidewire to ream the bone surface.

10. The method of claim 9, wherein engaging the reamer onto the guidewire includes moving the reamer along the guidewire during reaming until the reamer reaches a location on a distance scale acting as the relative location indicator.

11. The method of claim 8, wherein engaging the orthopedic tool onto the guidewire includes engaging the orthopedic tool in a close fit with a portion of the distal guidewire end.

\* \* \* \* \*